(12) United States Patent
Schouenborg

(10) Patent No.: US 8,386,006 B2
(45) Date of Patent: Feb. 26, 2013

(54) MEDICAL ELECTRODE, ELECTRODE BUNDLE AND ELECTRODE BUNDLE ARRAY

(75) Inventor: Jens Schouenborg, Lund (SE)

(73) Assignee: Neuronano AB (SE)

( * ) Notice: Subject to any disclaimer, the term of this patent is extended or adjusted under 35 U.S.C. 154(b) by 274 days.

(21) Appl. No.: 12/747,343

(22) PCT Filed: Dec. 3, 2008

(86) PCT No.: PCT/SE2008/000680
§ 371 (c)(1),
(2), (4) Date: Jul. 28, 2010

(87) PCT Pub. No.: WO2009/075625
PCT Pub. Date: Jun. 18, 2009

(65) Prior Publication Data
US 2011/0009728 A1    Jan. 13, 2011

(30) Foreign Application Priority Data
Dec. 10, 2007  (SE) ........................ 0702740

(51) Int. Cl.
*A61B 5/04* (2006.01)
*A61N 1/05* (2006.01)

(52) U.S. Cl. ......... 600/373; 600/377; 600/378; 607/116
(58) Field of Classification Search ................. 600/373, 600/377, 378; 607/116
See application file for complete search history.

(56) References Cited

U.S. PATENT DOCUMENTS

| | | | |
|---|---|---|---|
| 5,716,391 A * | 2/1998 | Grandjean | 607/127 |
| 6,091,979 A * | 7/2000 | Madsen | 600/377 |
| 6,419,868 B1 * | 7/2002 | Johnson et al. | 264/249 |
| 7,689,260 B2 * | 3/2010 | Finch et al. | 600/378 |
| 2002/0128700 A1 | 9/2002 | Cross, Jr. | |
| 2003/0158545 A1* | 8/2003 | Hovda et al. | 606/32 |
| 2004/0127968 A1 | 7/2004 | Kuzma et al. | |
| 2004/0199235 A1* | 10/2004 | Younis | 607/116 |
| 2007/0129770 A1 | 6/2007 | Younis | |

FOREIGN PATENT DOCUMENTS

| WO | WO 2005/007238 A1 | 1/2005 |
|---|---|---|
| WO | WO 2007/040442 | 4/2007 |
| WO | WO 2008/091197 A1 | 7/2008 |

OTHER PUBLICATIONS

International Search Report dated Mar. 2, 2009, issued in corresponding international application No. PCT/SE2008/000680.

* cited by examiner

*Primary Examiner* — Lee S Cohen
(74) *Attorney, Agent, or Firm* — Ostrolenk Faber LLP

(57) ABSTRACT

A medical microelectrode includes portions capable of movement relative to each other when implanted in or inserted into soft tissue, so as to increase or decrease their distance along the electrode. The electrode is at least partially embedded in a substantially rigid biocompatible matrix that is soluble or biodegradable a body fluid. Also disclosed are uses of the microelectrode; microelectrode bundles and arrays of microelectrode bundles and their uses; methods for inserting or implanting microelectrodes, microelectrode bundles and arrays of microelectrode bundles in soft tissue.

25 Claims, 11 Drawing Sheets

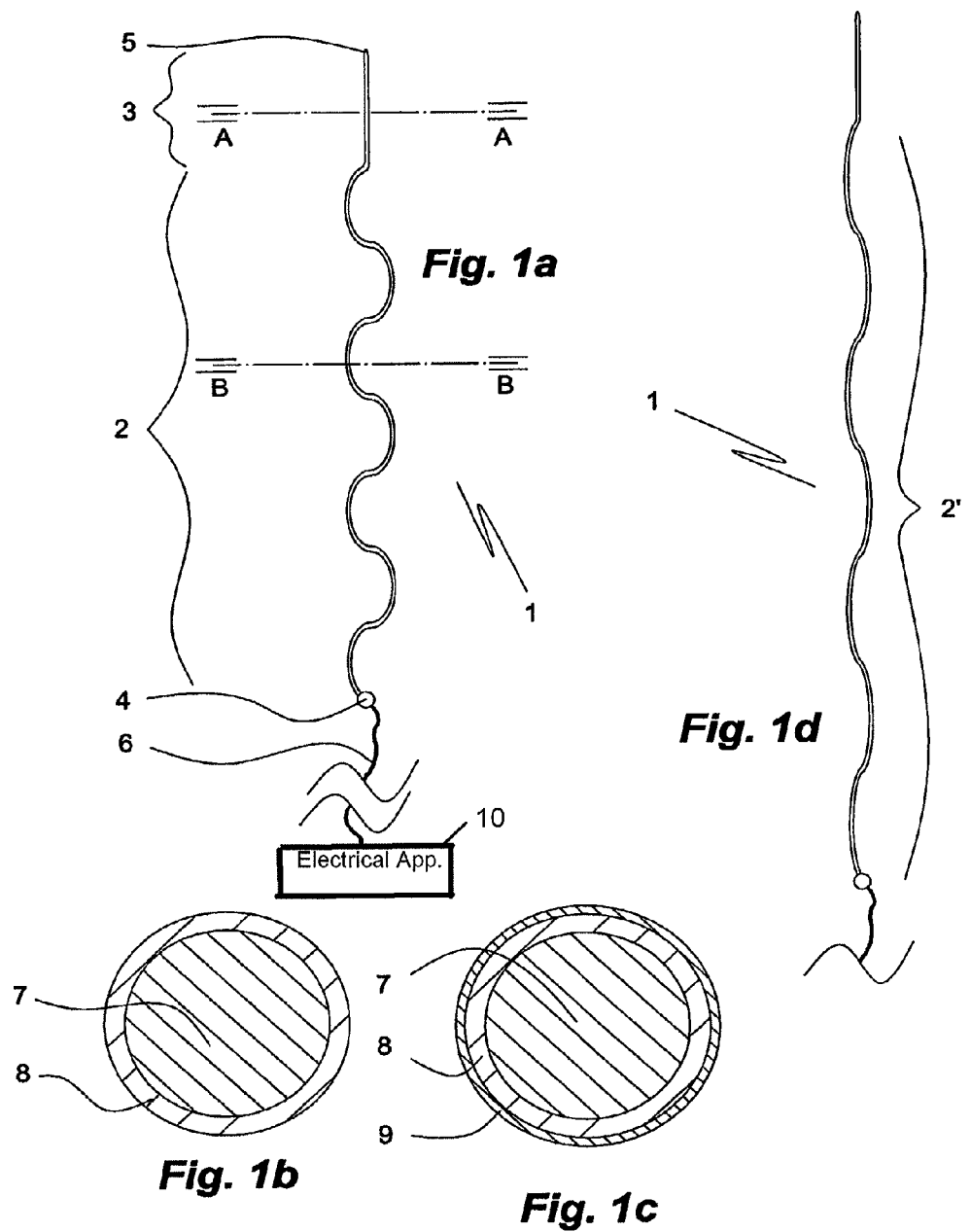

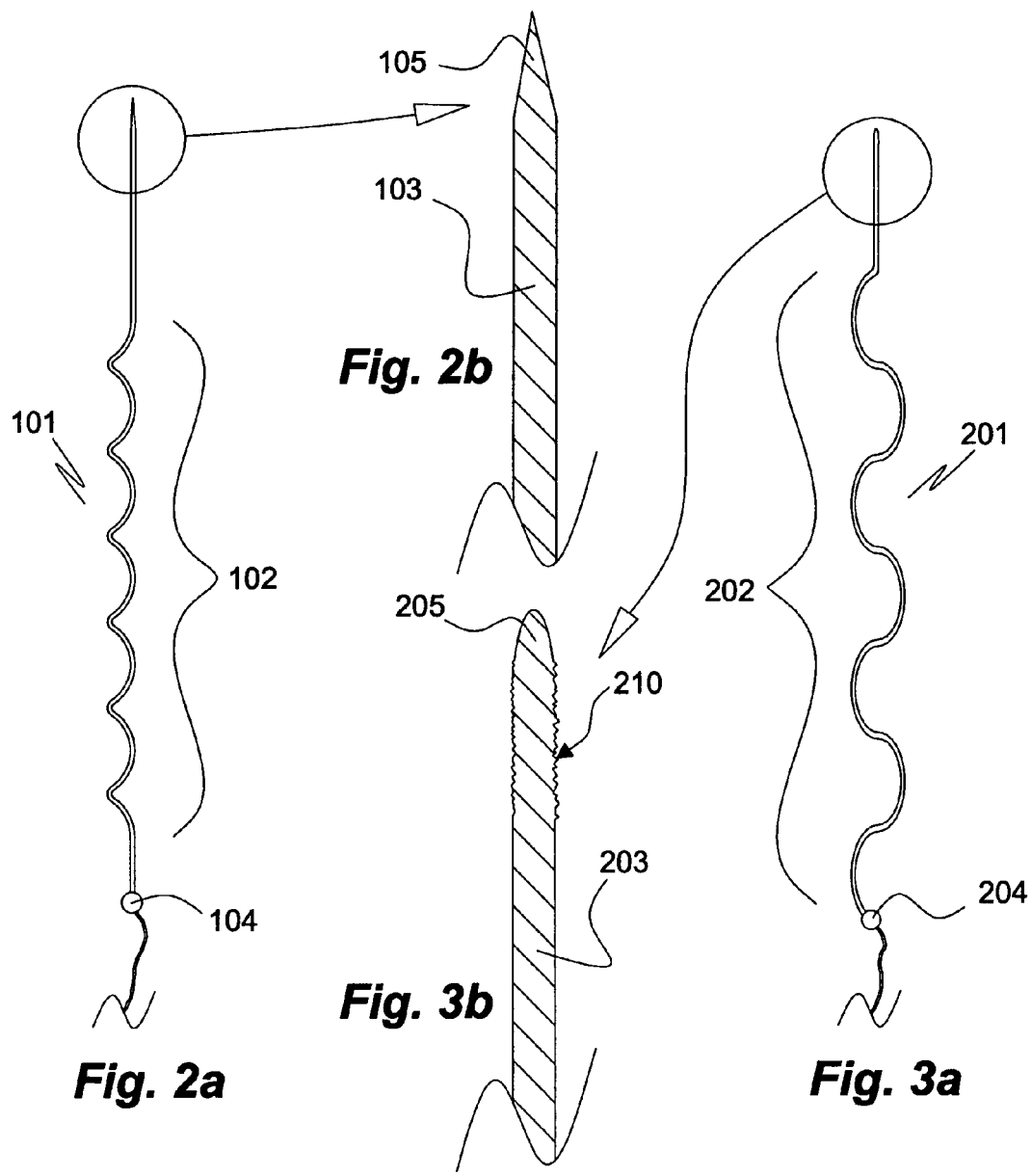

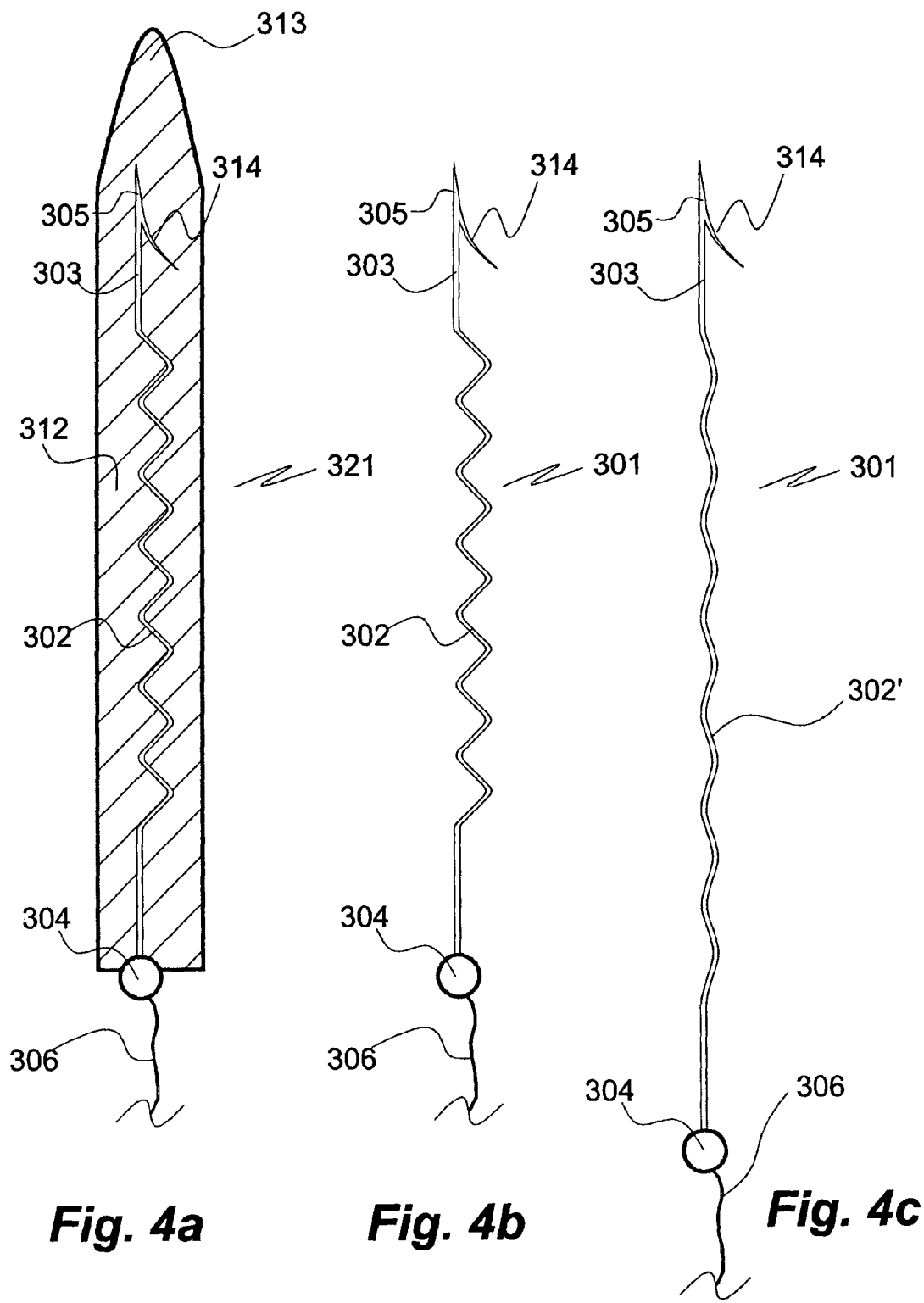

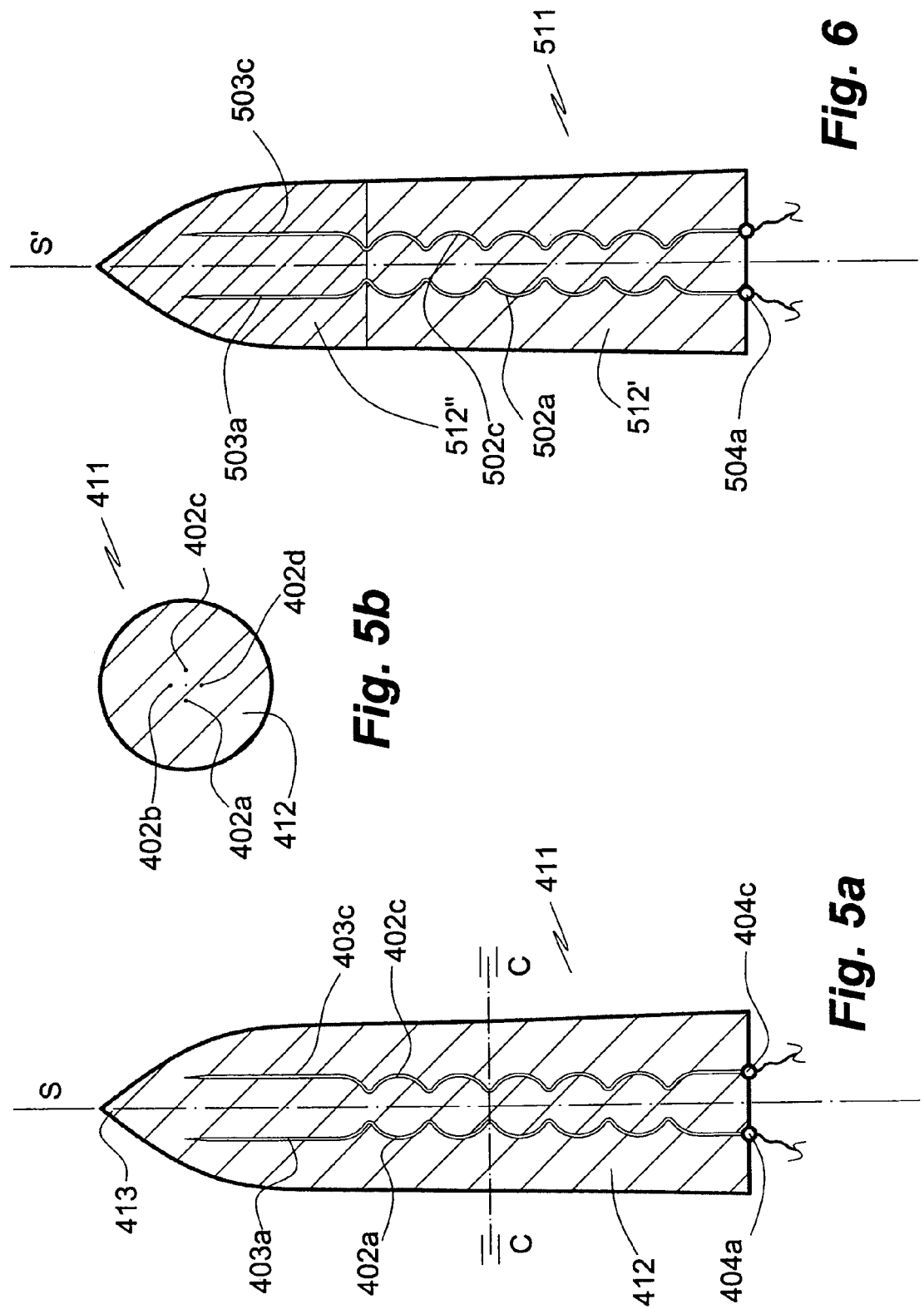

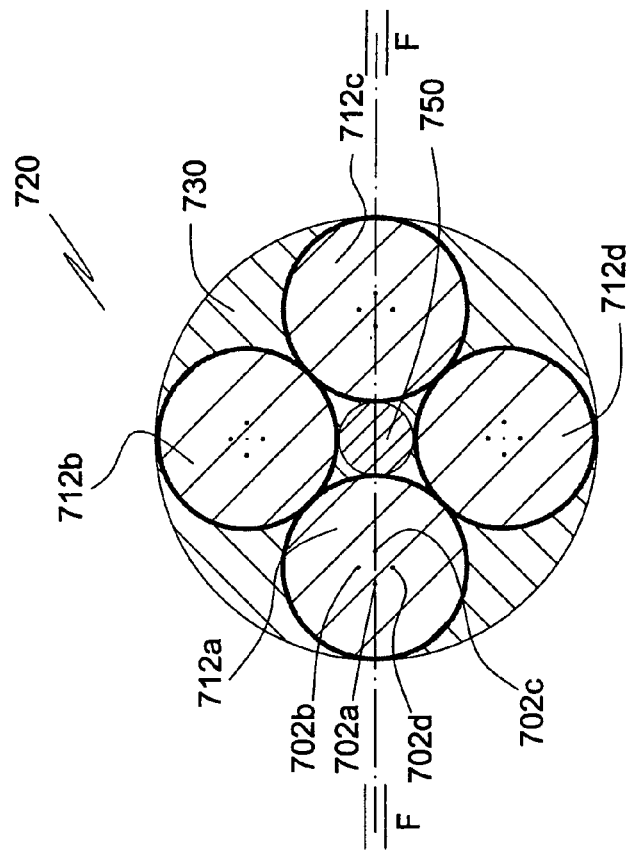
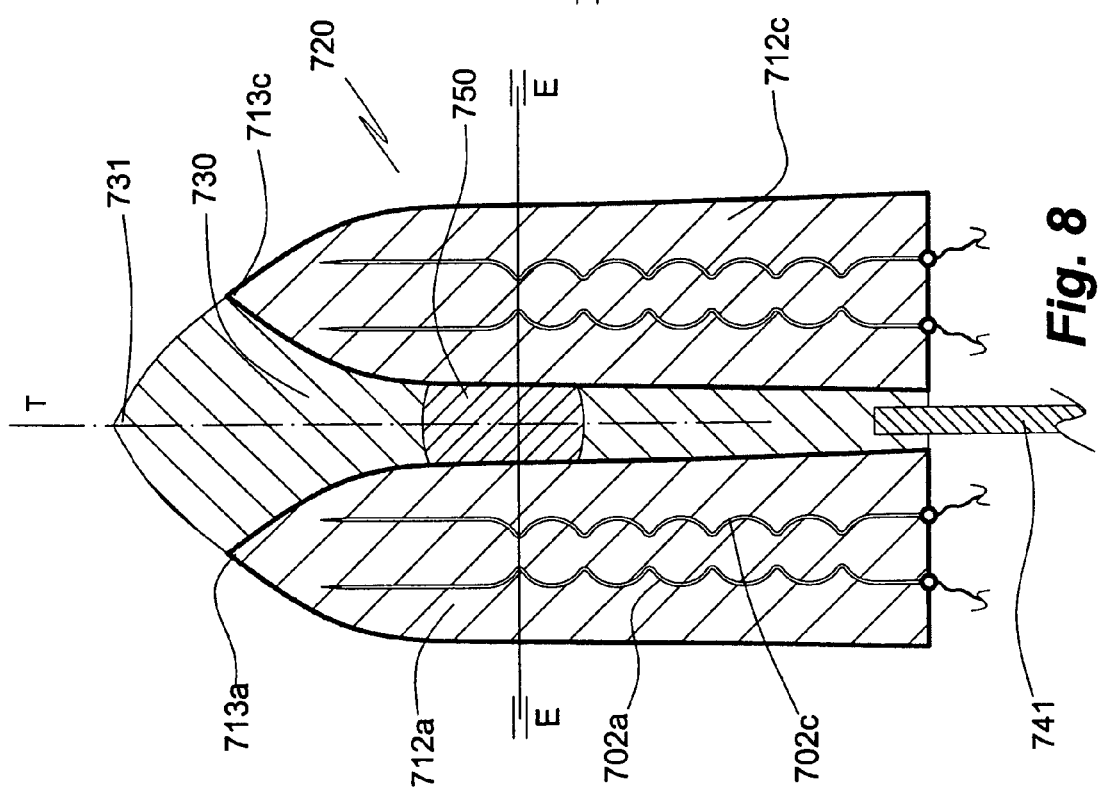

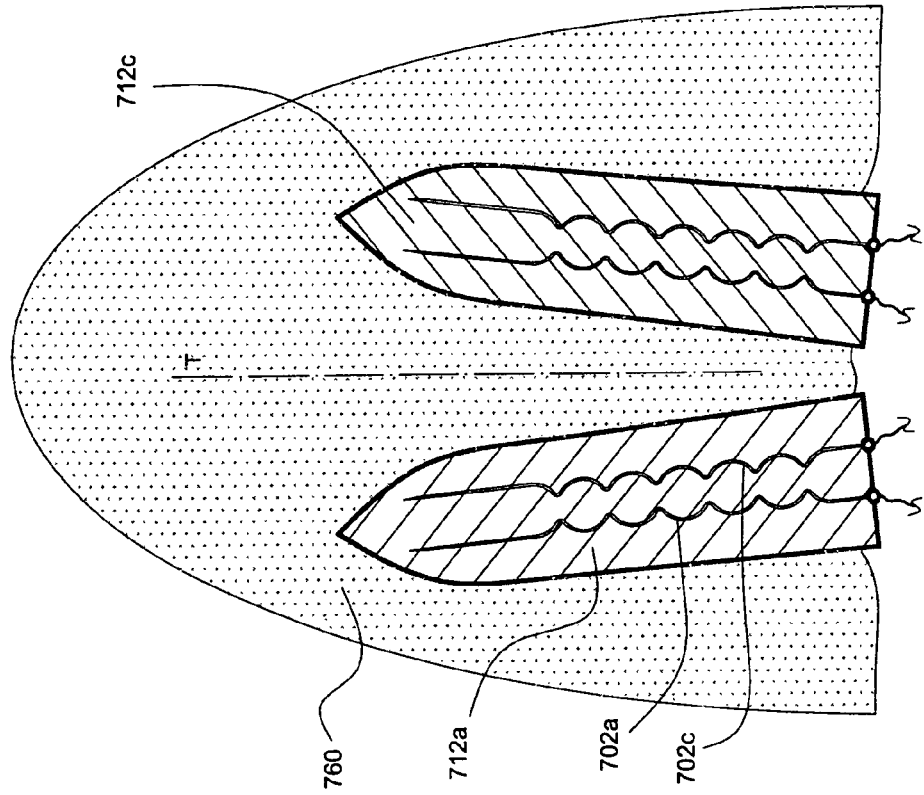
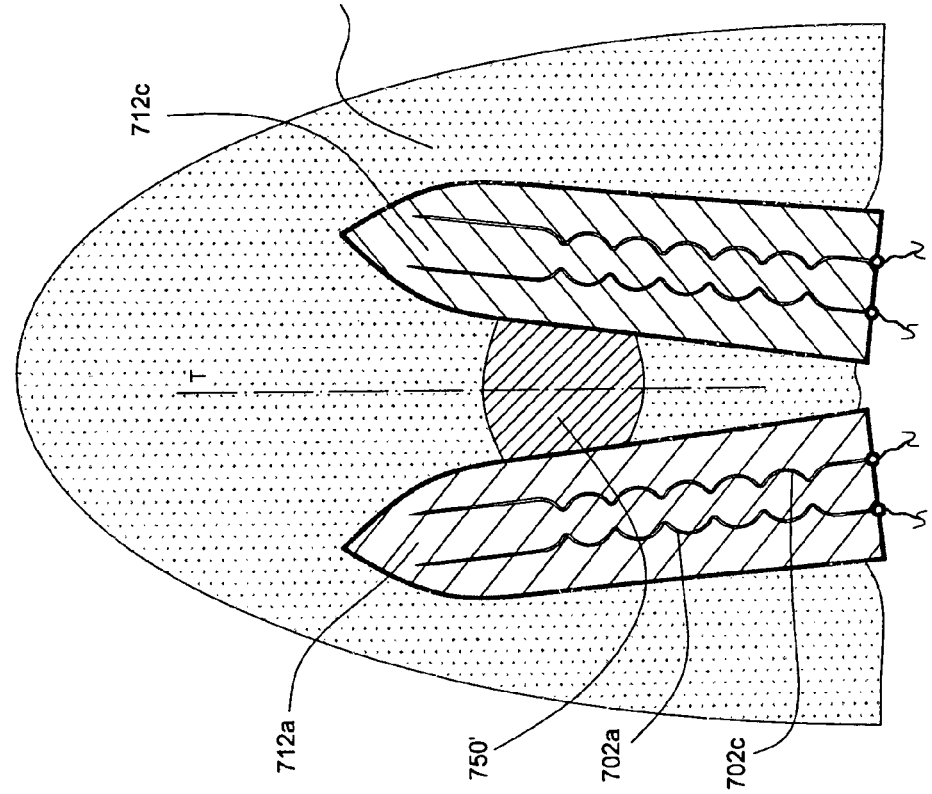

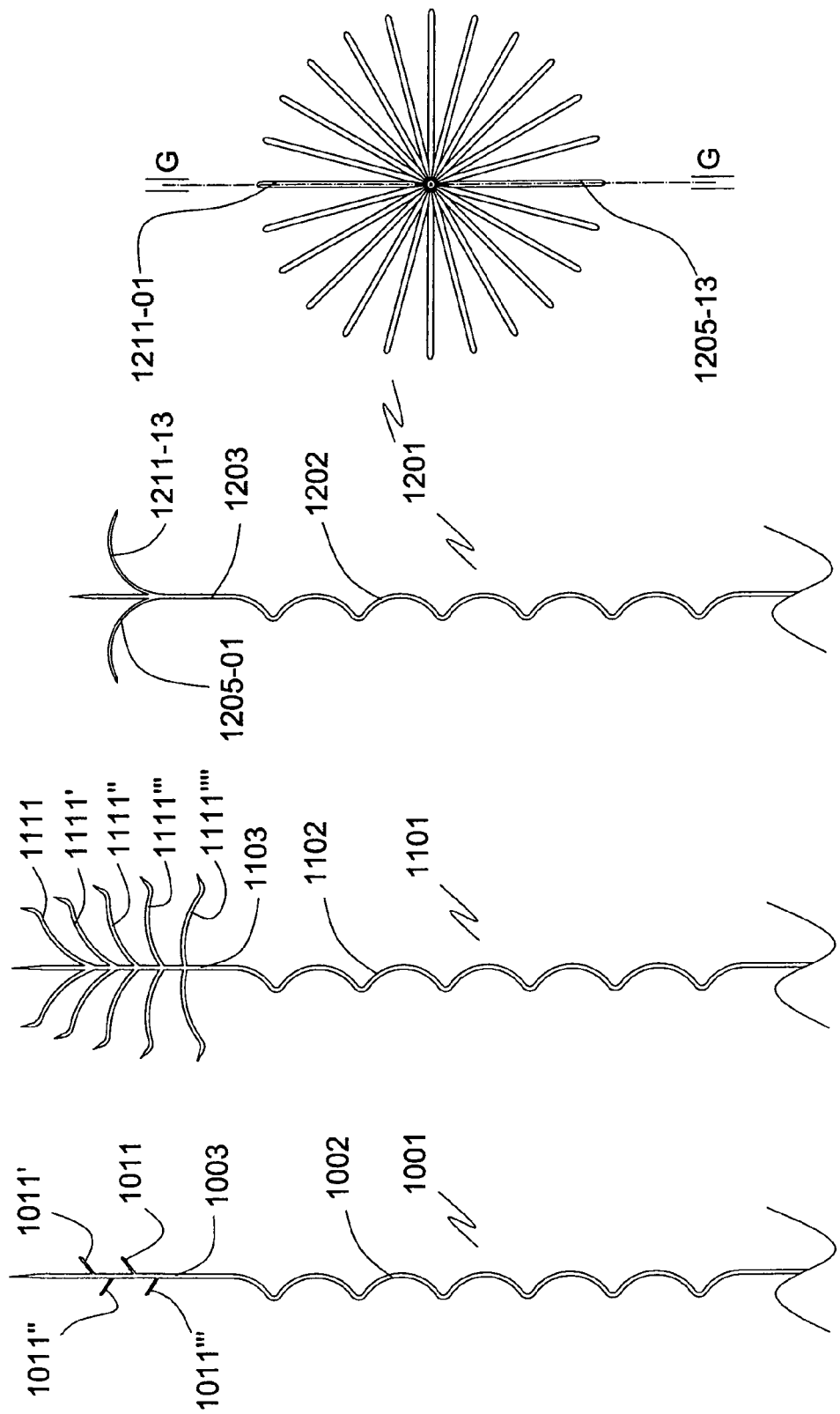

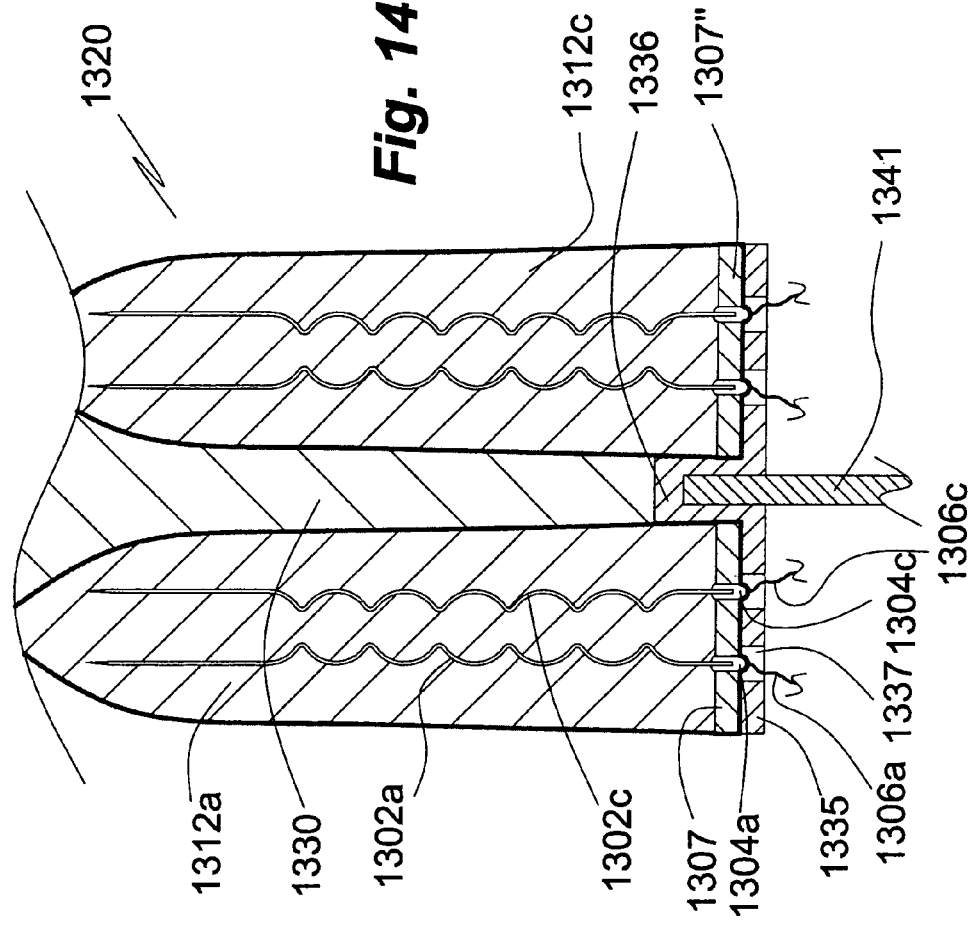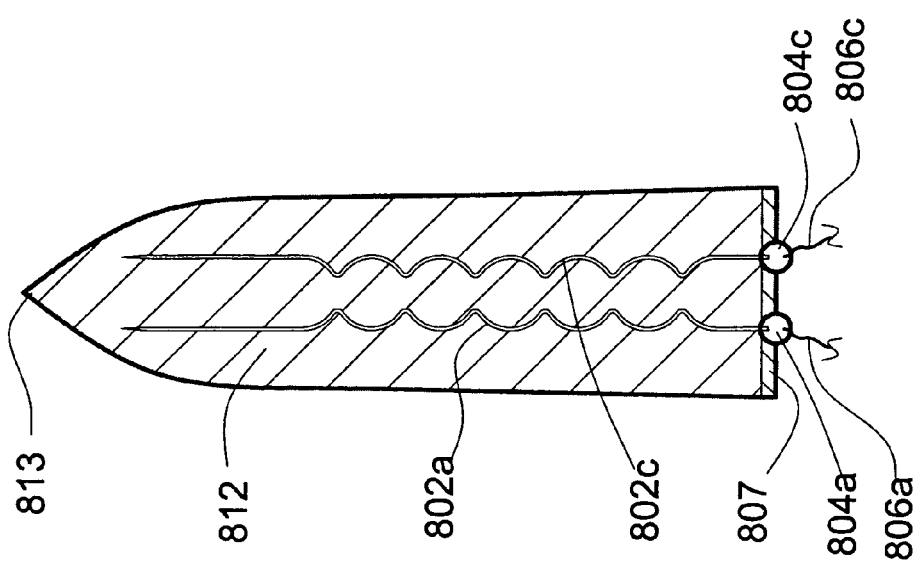

US 8,386,006 B2

MEDICAL ELECTRODE, ELECTRODE BUNDLE AND ELECTRODE BUNDLE ARRAY

CROSS REFERENCE TO RELATED APPLICATIONS

The present application is a 35 U.S.C. §371 National Phase conversion of PCT/SE2008/000680, filed Dec. 3, 2008, which claims benefit of Swedish Application No. 0702740-2, filed Dec. 10, 2007, the disclosure of which is incorporated herein by reference. The PCT International Application was published in the English language.

FIELD OF THE INVENTION

The invention relates to a medical electrode, in particular a medical microelectrode, to a bundle of such electrodes, and to an array of such electrodes and/or electrode bundles. The medical electrode, the electrode bundle and the array of electrodes or electrode bundles of the invention are intended for insertion into soft tissue such as the brain, the spinal cord, endocrine organs, muscles, and connective tissue.

BACKGROUND OF THE INVENTION

Electrodes that can be implanted for a long time into the central nervous system (CNS) have a wide field of application. In principle, all brain nuclei can be recorded from or stimulated by such electrodes and their functions monitored. Of particular importance is the use of a multi-channel design in brain nuclei stimulation. In such a design groups of electrodes or even individual electrodes can be addressed separately. This allows the user to select those electrodes the stimulation of which produces a therapeutic effect that is improved in comparison with unselective stimulation. Stimulation of the brain or spinal cord can be of particular value in situations when brain nuclei are degenerated or injured. Monitoring brain activity can be useful if linked to drug delivery or other measures such as electrical stimulation. Electrodes can also be used to lesion specific sites in tissue. To record and stimulate brain structures various forms of implanted electrodes have been developed and used in the past. To achieve durable implants of electrodes it is important to anchor the electrode in the tissue and minimize the movements of the electrode in relation to the tissue. Importantly, due to endogenous movements caused by e.g. breathing and ventilation or other movements, such as a sudden acceleration or deceleration of the body, different tissues such as the brain and the skull and even different parts of the same tissue, such as different sites within the brain or the spinal cord, may move relative to each other. For example, each heart beat causes a non-uniform or radiating movement around the arteries. When a straight and non-elastic wire runs through an area that is not moving uniformly, the wire will tend to slide within the tissue, thus causing mechanical friction with and/or altered tension within the surrounding tissue, which in turn may injure the tissue. Such movements will reduce the quality of recordings/stimulations that can be obtained with the electrode and may also cause a tissue reaction to the electrode. Another consideration of relevance to the present invention is that the anchoring properties of a wire electrode in a tissue are critical for optimal performance. Anchoring means arranged near the tip of wire electrodes in form of protruding filaments (barbs) are known. Tissue movements affecting a wire electrode will be propagated to the anchoring means, resulting in the risk of injury to adjacent tissue.

OBJECTS OF THE INVENTION

A first object of the invention is to provide an electrode of the aforementioned kind, which is adapted to move with the tissue into which it has been inserted or in which it has been implanted without being easily dislocated.

A second object of the invention is to provide an electrode of the aforementioned kind that does no or little harm to the tissue into which it has been inserted or in which it has been implanted.

A third object of the invention is to provide an electrode of the aforementioned kind, which can be easily positioned in a desired configuration in a desired location in soft tissue.

A fourth object of the invention is to provide a bundle of electrodes having the aforementioned desired properties.

A fifth object of the invention is to provide an array of electrodes and/or electrode bundles having the aforementioned desired properties.

Further objects of the invention will become evident from the following summary of the invention, a number of preferred embodiments illustrated in a drawing, and of the appended claims.

SUMMARY OF THE INVENTION

The present invention is based on the insight that it is desirable to improve the freedom of movement of different portions of a medical electrode, in particular a medical microelectrode implanted or inserted into soft tissue so as to avoid negative effects of non-uniform movements of surrounding tissue on the electrode, in particular effects tending to dislocate the electrode and/or to make it move in a manner that risks to cause damage to the surrounding tissue. In particular, the present invention is based on the insight that it is advantageous for such an electrode to comprise portions capable of movement relative to each other so as to increase or decrease their distance along the electrode. The invention is also based on the insight that, for their implantation or insertion, in particular their implantation or insertion in a desired configuration, the electrode of the invention, independent of whether pertaining to an electrode bundle or an array of electrode bundles or an array of single electrodes and electrode bundles or not, does require configurational stabilization. In this application, "configuration" relates to the three-dimensional forms or states that an electrode of the invention can assume or be forced to assume due to its flexibility. According to the invention configurational stabilization is provided by at least partial embedment of the electrode in a biocompatible support material that can be removed once the electrode has been disposed in a desired location in soft tissue. For easy removal, the support material is one that is dissolvable or degradable in body fluids, that is, in an aqueous environment but also, if the electrode is inserted into fatty tissue, in an environment that it rich in fat. After dissolution or degradation the support material or degradation products thereof, respectively, is cleared from the insertion site by solute transport mechanisms operating in living tissue and/or is metabolized. The support material of the invention may be one that needs to be degraded to make it soluble or to enhance its solubility in body fluids; such degradation is effected by mechanisms operative in living tissue.

Single Electrodes

According to the invention is disclosed an electrically conductive thin, flexible electrode for insertion into or implantation in soft tissue, the electrode having a first end and a second end and a configuration permitting the distance from its first end to its second end to be increased and/or decreased once implanted in tissue. At its first end the electrode comprises a base for electrical connection with an electrical apparatus by means of a flexible lead fastened to the base. The base may have any form suitable for that purpose. At its second end, the electrode comprises a tip section, in particular one adapted for insertion of the electrode into soft tissue and for optional anchoring of the electrode in tissue. The electrode body extending between the tip section and the base is flexible, optionally resiliently flexible, or comprises flexible portions and, optionally, resiliently flexible portions. The electrode body, which is preferably about circular in cross section, comprises an electrically conducting or non-conducting core, an electrically conducting layer on the core if the core is non-conducting, and an insulating layer on the electrically conducting layer or core. However, other electrode cross sections, such as rectangular or polygonal, may also be used. Alternatively, the electrode body comprises or consists of a non-conducting polymer tube filled with an electrically conducting material. A non-conducting core is preferably a natural, semi-synthetic or synthetic polymer filament, such as a filament of silk, cotton, artificial silk (cellulose acetate), polyethylene, polypropylene, polyamide, etc. A conducting core is a thin metal wire of gold, platinum, titanium, an alloy, steel or an electrically conductive polymer fibre. The electrically conducting layer on a non-conducting core consists or comprises a metal of high electrical conductivity, such as copper, silver, and gold or a metal alloy, e.g. platinum-iridium, deposed on the core by, for instance, ion sputtering or evaporation techniques. In case of a gold layer adhesion to the core can be improved by interposition of a chrome or tungsten layer between the gold layer and the core. Such interposition is also feasible with other metal layers. The thickness of a deposed metallic conductive layer is from 0.1 μm to about 100 μm. Alternatively, the electrically conducting layer may consist or comprise an electrically conducting polymer. The insulating layer comprises or preferably consists of an electrically non-conducting polymer. In most applications, the diameter of the electrode body is from about $10^{-7}$ to about $10^{-4}$ m, preferably less than about $2.5 \cdot 10^{-5}$ m. However, in some applications the electrode body may have a larger diameter, in particular if the electrode is intended for producing lesions of soft tissue.

The insulation layer of the electrode body extends preferably from the body's first end to the body's second end, that is, the entire electrode body is insulated. Examples of materials suitable for insulation are glass, polyvinyl formal, silicon rubber or a water-resistant lacquer. It is however possible to provide along the electrode body passages through the insulation layer to the conducting core, in particular passages disposed about perpendicular to the core.

If electrical stimulation of a larger volume of tissue is intended, it may be preferred not to insulate the portion of the electrode that is to be inserted into the target tissue. Alternatively, the electrode body may comprise regions that are not insulated to allow stimulation/recordings of multiples sites within the tissue.

To facilitate insertion into tissue the electrode of the invention is at least partially embedded in a rigid or substantially rigid body of a biocompatible matrix material. The matrix material of the invention is preferably macroscopically uniform. The embedment comprises at least a portion of the electrode body, more preferred the electrode tip and a portion of the electrode body extending from the tip. "Substantially rigid" indicates that the body may be only slightly resiliently flexible. The matrix body comprises or consists of a solid matrix material that is soluble or biodegradable in a body fluid, in particular an aqueous body fluid but, alternatively, also in one rich in fat. Incorporation of the electrode in the matrix body not only allows the electrode to be inserted or implanted into tissue and to be disposed therein in a desired disposition but also in a desired configuration. The electrode or at least portions thereof are configurationally locked in the matrix. After dissolution or degradation of the matrix the electrode, in particular the electrode body, may retain its initial or first configuration in tissue or assume or made to assume a second configuration or an unlimited number of configurations. By "initial configuration" is meant the configuration of the electrode or the electrode body or a section of the electrode body in a matrix. A curvy or other non-straight shape of the electrode body improves the anchoring of the electrode in tissue, since tissue cells will grow close to the body. In contrast to a straight electrode body, a curvy or other non-straight electrode body does improve the ability of the electrode of the invention to move, without being dislocated, in unison with non-uniform movements of the tissue into which the electrode is implanted or inserted.

The adoption of a second configuration by the electrode body can be provided by several means. If the electrode body is resiliently flexible or comprises resiliently flexible portions it may be embedded in the matrix body in a compressed or tensioned state so that, upon dissolution of the matrix after implantation of the electrode in soft tissue, the electrode body may expand or contract, respectively.

In its initial configuration the electrode body, while generally extending in one direction, may comprise regular or irregular bends, spirals, loops, zigzag sections, etc. In other words, in its initial conformation, the length of the electrode body is substantially greater than the distance between its first and second ends. By substantially greater is meant a length such as by 2 percent or more, in particular by 5 percent or more, even by 20 percent or more, and up to by 50 percent or more, of the distance between its first and second electrode ends. The tip section of the electrode extending from the second end however preferably has a straight or slightly bent configuration.

The distal end or tip section of the electrode, which is not insulated, can be of any suitable shape. Sharp tips are preferred if the electrode is intended for recording purposes. If the electrode is intended to be used for stimulation it is preferred that the electrode tip section does not comprise sharp edges but rather has a smooth contour to reduce the erosion of the tip section. Optionally the surface area of the electrode tip section may be enlarged by roughening to increase the contact with surrounding cells and decrease the impedance of the electrode. A rough surface can be obtained by, for instance, coating the electrode with platinum black or by etching.

At its base, the electrode is in electrically conductive contact with electronic equipment via an insulated flexible electrical wire.

At its tip and/or its body section the electrode of the invention can advantageously be provided with anchoring means, such as rough surface portions or surface portions having adhesive or properties or in respect of surrounding tissue. They may even be of a kind, for instance of titanium or having portions coated with titanium oxide, allowing tissue adhesion or ingrowth. Thin laterally extending filaments attached to the tip section, which are disposed in a proximal direction during the insertion procedure and then unfold on retracting the electrode for a short distance, are known (WO 2007/040442); the electrode of the invention may be provided with such filaments to further anchor it in tissue. It is preferred that these thin laterally extending filaments have a diameter equal to or preferably less than the diameter of the electrode body, and/or to be of a length to allow them to laterally protrude for a suitable distance, such as up to fifty μm or more, and even up to hundred μm or more, from the electrode. It is preferred for the laterally extending filament(s) to additionally function as electrodes, in which case at least their tip is not insulated. It is also preferred for a laterally extending filament to comprise or consist of the electrically conductive material of the electrode, and for that material to be integral with the material of the electrode body. It is however also within the scope of the invention that the lateral extending filaments are of a material different from that of the electrode. Since the laterally extending filaments do not hinder insertion of the matrix-embedded electrode into tissue, they may extend from the electrode in any direction, such as a distal, radial or proximal direction. It is also possible for an electrode to comprise a multitude of laterally extending filaments and for those filaments to extend in one or several directions from the electrode. Likewise, it is preferred for the core or supporting tube of the electrode to be of the same material as the tip section and to be integral with it. In an electrode equipped with protruding elements at its tip section such withdrawal may allow the protruding elements to become anchored in the tissue and to make the electrode resist withdrawal. Pushing an electrode of appropriate tip design, such as a tip bending or slanting away from the long axis of the electrode body defined by the straight line connecting its first and second ends further into the tissue may cause its tip portion to deviate sideways from the direction of the long axis.

The matrix body of the invention is of a biocompatible material that dissolves or is degraded in a body fluid, in particular an aqueous environment but, alternatively, also in an environment rich in fat. The degradation may be catalyzed by enzymes present in a body fluid in contact with the matrix, in particular an aqueous body fluid or body fat. Prior to dissolving or being degraded, the matrix body may swell or not. The matrix body is preferably oblong in a distal direction, that is, forms the frontal part of the matrix-embedded electrode that is first introduced into the tissue. It can be shaped, for instance, as a bar of a length at least equal to the distance between the first and second ends of the electrode in its initial conformation. The matrix body is preferably tapering in the direction of its distal end. Its distal end section is preferably about conical to facilitate insertion into soft tissue. Its distal tip may have a sharp or a blunt shape. A blunt shape minimizes the risk of vascular rupture during insertion while a sharp tip will reduce the resistance of the tissue against insertion. The shape of the matrix body permits to follow a straight insertion track line when inserting the electrode deep into the soft tissue, and thereby enables the user to accurately position the electrode in the tissue. Suitable matrix materials include biocompatible carbohydrate based or protein based gluing materials known in the art. Other useful known biocompatible matrix materials include: polyglycolic acid, carboxyvinyl polymer, sodium polyacrylate, carboxymethyl cellulose, sodium carboxymethyl cellulose, pullulan, polyvinylpyrrolidone, karaya gum, xanthane gum, gum Arabic, gum Guar, gum *Cassia* Tora, gum Ghatti and other natural gums, pectin, tragacanth, alginic acid.

Optionally, the matrix body comprises two or more sections of matrix materials differing in their dissolution or degradation rate in a body fluid, in particular an aqueous environment but even in an environment rich in fat. For example, in certain applications it is advantageous for the matrix body to comprise or consist of two sections, a proximal section and a distal section, wherein the dissolution rate of the material of the distal section is substantially higher than that of the material of the proximal section, so as to shorten the dissolution time of the distal section by from twenty seconds to ten minutes. This design enables the electrode of the invention to be inserted close to the target tissue with both matrix sections intact; upon dissolution of the matrix material of the distal section, in which a distal or second end portion of the electrode body and/or the tip section is embedded, the electrode may be withdrawn from the tissue by a short distance or pushed further into the tissue by a short distance. It is within the ambit of the invention for the matrix body to comprise a dissolution enhancing means such as channels that can be infiltrated by body fluid. Thus the matrix body or a portion thereof may have non-porous or a porous structure. Retardation of the dissolution or degradation of the matrix material can be achieved by arranging one or more layers of a dissolution retardation or a degradation retardation coating on the matrix body or on sections thereof. The matrix dissolution or retardation coating is of a material that preferably dissolves in an aqueous environment at a rate substantially slower that that of the matrix section protected by it. The matrix dissolution retardation coating may also be one that is not readily dissolvable but is degradable in an aqueous environment or an environment rich in body fat, such as a wax coating, a polyester coating, for instance a polyglycolate, polylactate, poly (glycolate, lactate) or polycarbonate coating or a peptide coating, such as a coating of collagen.

The electrode of the invention is intended for insertion into soft living tissue, in particular brain and spinal cord tissue, but also, for instance, into the liver, the kidneys, skeletal muscles, heart muscles, visceral muscles, and connective tissue. The electrode of the invention can be used for recording and/or for nerve-stimulating purposes. If used for recording purposes, an electrode wire of the invention can be equipped with a miniaturized preamplifier. It is preferred for the amplifier to be arranged at a short distance from the tip, such as at the junction of the body and tip sections, to improve the signal to noise ratio.

To further facilitate insertion into soft tissue, it is preferred that a micro-manipulator rod or similar is attached to the matrix or embedded in the matrix near or at the proximal end thereof. Releaseable attachment of the micro-manipulator may alternatively be provided by a docking means fixed to the base section of the electrode.

The present invention thus discloses a flexible electrode the length from the distal tip to the proximal base of which can be reversibly increased and decreased following insertion into soft tissue.

Electrode Bundles

In certain applications it is an advantage to use multiple, suitably arranged electrodes of the kind disclosed above. For example, the rigid or substantially rigid matrix body of the invention can be shared by two or more electrodes, even up to hundreds of electrodes, with the aim of disposing a plurality of electrodes in a soft tissue region. The combination of two or more electrodes of the invention in a common matrix body is termed "electrode bundle". It is also within the ambit of the invention to provide an electrode bundle with conventional straight electrode wires, optical wires, contractile polymers or stiff electrode chips containing electrodes and/or electronics, which elements are at least partially disposed in the matrix body. Optionally, the matrix body comprises two or more sections of matrix materials differing in their dissolution rate in an aqueous environment. A sectioned matrix body for an electrode bundle of the invention corresponds in respect of its features to the matrix body of the electrode of the invention described above.

It is preferred for the electrodes of the invention comprised by the electrode bundle to be of varying length and, if the matrix body is of rotationally symmetric form, for instance cylindrical, to be arranged around the central axis thereof. It is preferred for the longest electrodes to be disposed at a short distance from the axis and for the shorter ones at a greater distance from the axis so as to make their tips define a rounded matrix body tip. Their proximal ends are preferably disposed in or near a plane transverse to the rotational axis. It is however also within the scope of the invention to arrange the electrodes in a manner forming a unilaterally slanting or otherwise not symmetric electrode bundle tip. Thus the electrode bundle matrix body may be tapering in a distal direction so as to form, for instance, a conical or flat triangular terminal distal portion. The terminal distal portion can have a blunt shape to minimize the risk of vascular rupture during insertion of the electrode bundle into soft tissue.

According to another preferred aspect of the invention the electrode bundle comprises one or more optical fibres to allow radiative stimulation of the tissue or components thereof and/or for recording radiation emanating from surrounding tissue. In a manner corresponding to that of the electrodes the one or more optical fibres are kept in a selected position in the electrode bundle by means of the matrix.

According to a further preferred aspect of the invention two or more electrodes in the matrix-embedded electrode bundle of the invention can be joined at or near their first ends by a base plate of, for instance, a ceramic or polymer material. Electrodes so joined may be of same or different length. The base plate may be equipped with electronic components such as amplifiers and be connected to electronics outside the tissue for stimulation and recording purposes via a cable or telemetrically; it may also be used for mounting a' means for receiving a micromanipulator.

According to a still further preferred aspect of the invention the electrode bundle comprises one or more contractile bimetallic elements capable of changing their shape, for instance to bend, when electric current is passed through them. Such contractile elements can be used to control the insertion path of the matrix-embedded electrode bundle.

For insertion of the electrode bundle into soft tissue a micromanipulator is attached or attachable to a proximal end portion of the electrode array, from which it extends in a proximal direction.

The stiffness of the electrode bundle of the invention facilitates its insertion into tissue. Upon insertion, the first matrix section is quickly dissolved. Thereby the distal terminal portion of an electrode becomes capable of lateral displacement in respect of neighbouring electrodes. Further insertion of the electrode bundle into the tissue causes a distal portion of an electrode comprising a fanning-out means to bend, in an unfolding manner, in a direction away from the axis of the electrode bundle. Dissolution of the second matrix portion frees the proximal portion of an electrode so that it becomes capable of lateral and/or axial displacement in relation to neighbouring electrodes and to assume a floating disposition in the tissue; thereby its position in the tissue is stabilized and tissue reactions or injuries that otherwise would have occurred due to its joint movement with other electrodes be prevented.

Arrays of Electrodes and/or Electrode Bundles

According to the invention two or more matrix-embedded electrodes and/or electrode bundles disposed in parallel or about in parallel can be joined by a glue that dissolves in an aqueous medium such as a body fluid. The glue must be biocompatible. Suitable glues can be glues on a carbohydrate or a protein basis, such as alkylated and/or carboxylated cellulose derivatives, amylose, and gelatin, but can also be of a different nature, such as polyvinylpyrrolidone and alkali salts of polyacrylic acid. In this manner electrodes and/or electrode bundles can be arranged in an array in a desired geometric pattern suitable for implantation. Thereby the time required for implantation is considerably shortened compared with that for the same geometric pattern obtained by implantation of individual electrodes and/or electrode bundles. One or more matrix-embedded electrodes and/or electrode bundles of the invention in such an array can be substituted by two or more of matrix-embedded electrodes of the invention that are temporarily or permanently kept in a fixed relationship in respect of each other. The means for keeping them in such fixed relationship may comprise or consist of one or more matrix materials of the invention or be independent thereof. If independent thereof, the means can be one that dissolves and/or disintegrates more slowly in an aqueous environment than any other matrix material of the matrix-embedded electrode bundle or a permanent one, such as a means keeping the electrode bundle of WO 2007/040442 in a fixed relationship. Similarly one or more electrode bundles in the electrode array of the invention can be substituted by one or more electrode bundles of WO 2007/040442. A suitable distance between electrode bundles in an electrode bundle array of the invention is from 50 µm to 500 µm or more.

The array of matrix-embedded electrode bundles or of a combination of matrix-embedded electrodes of the invention and matrix-embedded electrode bundles of the invention is suitable for long-lasting stimulation, multi-channel recordings of electrical neuronal activity and levels of transmitter substance or other bioactive molecules through measurements of redox reactions and precise lesions of the tissue for scientific, medical and animal care purposes.

Methods and Uses

According to the invention is also disclosed a method of manufacturing an electrode of the invention embedded in a matrix body. The method comprises providing a fixation means, fixing the electrode and, optionally additional elements to be imbedded, such as optical fibres, contractile elements, etc., in the fixation means in a desired configuration, applying a sheath covering the thus fixed electrode except for at the base thereof, applying a solution or suspension of a first matrix material on the electrode in a manner so as to cover the portions of the electrode intended to be embedded, allowing the solvent/dispersant of the matrix solution or suspension, respectively, to evaporate or harden, removing the sheath, and releasing the electrode from the fixation means. For embedment of the electrode in two matrix materials so as to form corresponding matrix compartments, each enclosing a portion of the electrode, an appropriate portion of the electrode fixed by a fixation means as described above is coated with a solution or suspension of the first matrix material, the solvent/dispersant of which is subsequently evaporated, followed by coating the portion of the electrode remaining to be coated with a solution or suspension of the second matrix material, subsequently evaporating the solvent/dispersant of the second matrix material, and releasing the electrode from the fixation means. In the method the electrode is preferably disposed in a sheath of smooth material of low wettability such as a polyfluorinated hydrocarbon polymer or silicon rubber, and fixed therein. To facilitate solvent evaporation the sheath material is advantageously porous, in particular microporous. After application and drying of the matrix material(s), the electrode is withdrawn from the sheath.

An alternative method of embedding an electrode of the invention into two matrix materials forming distinct matrix compartments into which portions of the electrode are embedded, comprises embedding the entire electrode in a first matrix material, dissolving a portion of the first matrix material, preferably a distal portion extending from the distal end, covering the now non-embedded distal portion of the electrode with a second matrix material by, for instance, taking recourse to a sheath applied on the non-embedded distal portion, filling the sheath with a solution or suspension of the second matrix material, evaporating the solvent so as to dry/harden the second matrix material, and removing the sheath.

According to the present invention is also disclosed a method of inserting or implanting a matrix embedded electrode, in particular the matrix embedded electrode of the invention, into soft tissue.

According to the present invention is also disclosed a method of inserting or implanting a matrix embedded electrode bundle, in particular the matrix embedded electrode bundle of the invention, into soft tissue.

According to the present invention is also disclosed a method of inserting or implanting an array of matrix embedded electrode bundles, in particular the array of matrix embedded electrode bundles of the invention, into soft tissue.

The invention also relates to the use of the matrix-embedded electrode, the matrix-embedded electrode bundle or the array of matrix-embedded electrode bundles for long-lasting nerve stimulation, multi-channel recordings of electrical neuronal activity and levels of transmitter substance through measurements of redox reactions and lesions of the tissue for scientific, medical and animal care purposes.

The invention will now be explained in more detail by reference to a number of preferred embodiments illustrated in a rough drawing comprising a number of figures, which are however not to scale. Electrode bundles are rendered with an enhanced contour.

DESCRIPTION OF THE FIGURES

FIG. 1a is a longitudinal section through a first embodiment of the electrode of the invention comprising a tip section and a body of a non-conductive silk core coated with silver and gold, and a polymer insulating coat, with the body in a wavy configuration;

FIGS. 1b and 1c are transverse sections A-A, B-B through the tip and body, respectively, of the electrode of FIG. 1a;

FIG. 1d is the embodiment of FIG. 1a, in an extended state;

FIG. 2a is a longitudinal section through a second embodiment of the electrode of the invention, in a state corresponding to that of the embodiment of FIG. 1a;

FIG. 2b is an enlarged partial view of the tip of the electrode of FIG. 2a;

FIG. 3a is a longitudinal section through a third embodiment of the electrode of the invention, in a state corresponding to that of FIG. 1a;

FIG. 3b is an enlarged partial view of the tip of the electrode of FIG. 3a;

FIGS. 4a-4c are longitudinal sections through a fourth embodiment of the electrode of the invention, shown embedded in a dissolvable matrix (4a), in a state after insertion into a soft tissue and dissolution of the matrix (4b), and in an extended state (4c) in the tissue;

FIG. 5a is a longitudinal section through a first embodiment of a bundle of electrodes of the invention embedded in a dissolvable matrix;

FIG. 5b is a transverse section C-C through the embodiment of FIG. 5a;

FIG. 6 is a longitudinal section through a second embodiment of a bundle of electrodes of the invention embedded in a combination of dissolvable matrices, in a view corresponding to the view of the bundle of electrodes in FIG. 5a;

FIG. 7b is a transverse section D-D through the electrode bundle array of FIG. 7a;

FIG. 8 is a longitudinal section F-F through a second embodiment of the electrode bundle array of the invention embedded in a combination of dissolvable matrices and comprising a swelling means;

FIG. 8a is a transverse section E-E through the electrode bundle array of FIG. 8;

FIGS. 8b-8f illustrate the process of consecutive dissolution of the dissolvable matrices of the array of FIGS. 8, 8a inserted into soft tissue, in the same view as in FIG. 8;

FIGS. 10-11 illustrate a fourth and a fifth embodiment of the electrode of the invention, in a view corresponding to that of FIG. 1a;

FIG. 12 illustrates a sixth embodiment of the electrode of the invention, in a longitudinal section G-G (FIG. 12a);

FIG. 12a is an enlarged top view, in a proximal direction, of the electrode of FIG. 12;

FIG. 13 is a longitudinal section through a further embodiment of a bundle of electrodes of the invention embedded in a dissolvable matrix and joined at their proximal ends by an electrode holder disk, in a view corresponding to the view of the bundle of electrodes in FIG. 5a;

FIG. 14 is a longitudinal section through a fourth embodiment of the electrode bundle array of the invention comprising four matrix-embedded electrode bundles of the kind shown in FIG. 13 mounted on an array holder disk, in a view corresponding to the view of the array of bundle of electrodes of FIG. 7 but with a portion of the distal end section omitted.

DETAILED DESCRIPTION OF THE INVENTION

Figure 7B:
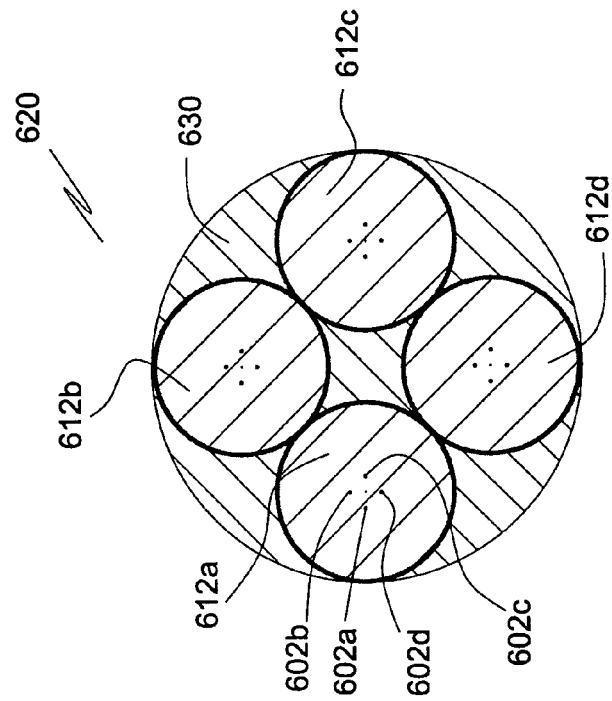

The first embodiment 1 of the electrode of the invention of FIGS. 1a-1c comprises a generally oblong waveform body 2 with a base 4 at its first, proximal end and a tip section 3 at its second, distal end with a point or tip 5, which may be sharp or blunt. A blunt tip 5 has the advantage of avoiding damaging blood vessels if disposed in a tissue rich in such vessels. The base 4 of the electrode 1 is a pearl of solder connecting the electrode body 2 at its proximal end with a thin insulated wire for electrical connection with an electrical apparatus 10. The electrical apparatus may be of various kind, such as for feeding electric current to the electrode and/or for receiving electrical signals from the electrode. The electrode body 3 is flexible but substantially not resilient. As shown in the enlarged transversal section of FIG. 1c it consists of a core 7, an intermediate layer 8, and a coat 9. The core 7 is a silk thread on which the thin intermediate layer 8 of chromium has been deposed by ion sputtering. The intermediate layer 8 is covered by a coat 9 of polyvinyl formal. In contrast to the electrode body 2 the tip section 3 is not insulated, that is, lacks the coat 9 (FIG. 1b). Applying a slight force to the opposite ends of the electrode 1 so as to draw it apart results in the extended, substantially straight configuration of the electrode body shown in FIG. 1d.

The second embodiment 101 of the electrode of the invention shown in FIGS. 2a, 2b differs from the first embodiment by the waveform pattern of its body 102. Reference nos. 103, 104 refer to the tip section, which ends in a sharp point 105, and to the electrode base, respectively.

The third embodiment 201 of the electrode of the invention shown in FIGS. 3a, 3b differs from the first embodiment by a roughened surface portion 210 of the tip section 203 extending from the blunt tip 205 in the direction of the wavy electrode body 202 and the electrode base 204. The roughening improves retention at the implantation site and increases the contact area of the electrode with surrounding cells, thereby lowering the electrical resistance between the electrode and the cells.

In FIG. 4a a fourth embodiment 301 of the electrode of the invention is shown with its tip section 303 and its body 302 embedded in a matrix shell 312 of water soluble material in a manner so that the sharp electrode tip 305 points in the same direction as the blunt matrix shell tip 313. At a distance from the tip 305 a barb 314 extends in a skew proximal direction from the tip section 303. Except for at its lead 306 bearing base 304 the electrode 301 is fully embedded in the matrix shell 312. The embedded electrode body 302 has a zigzag configuration. The combination 321 of electrode 301 and matrix shell 312 is termed "stabilized electrode". It is in this stabilized form 321 that the electrode 301 can be inserted into soft tissue while retaining its zigzag body configuration. Within a short time upon insertion the matrix shell 312 is dissolved by body fluid (FIG. 4b); the electrode 301 does however still substantially retain the zigzag configuration in which it had been embedded in the matrix shell 312 and in which it had been inserted into the tissue. By the barb 314 the electrode 301 is anchored in the tissue, in particular against a force seeking to withdraw the electrode 301 from it. By application of a withdrawing force to the base 304 the electrode body 302 can be straightened, viz. extended, to assume the straightened configuration 302' shown in FIG. 4c.

A first embodiment of a matrix-embedded bundle 411 of four electrodes of the invention is shown in FIGS. 5a, 5b. The electrodes, which are of the kind of the electrode 101 of FIGS. 2a, 2b, are disposed in parallel and equidistantly from the rotational axis S of the bundle 411 in a dissolvable matrix body 412. In respect of the electrode body 402a of the first electrode, the bodies 402b, 402c, 402d of the other electrodes are disposed in an angle of 90°, 180° and 240°, respectively. In FIG. 5a the tip sections 403a, 403c and the bases 404a, 404c of the first and third electrodes, respectively, are also shown. The generally cylindrically tapering matrix body 412 tapers in a distal direction, only slightly at start but more pronounced towards its distal pointed end 413.

The second embodiment of a matrix-embedded bundle 511 of four electrodes of the invention shown in FIG. 6 comprises four electrodes of the kind disclosed in FIGS. 2a, 2b and in the same disposition in respect of a rotational axis S' as in the matrix-embedded electrode bundle 411 of FIGS. 5a, 5b. In contrast to the embodiment of FIGS. 5a, 5b the matrix body comprises two sections, a proximal section 512' enclosing the electrode bodies 502a, 502c, etc., and a distal section 512" enclosing their tip sections 503a, 503c. The dissolution rate of the proximal matrix body section 512' is slower than that of the distal matrix body section 512". This allows insertion of the entire matrix-embedded bundle 511 to a desired first depth or level of a soft tissue and, upon dissolution of the distal section 512" material further insertion to a second depth or level, during which the now unsupported tips sections 503a etc. of the first electrode 502a, 503a, 504a and of the other electrodes are no longer immobilized but may bend, for instance bend away from the central axis S'.

Figure 7A:
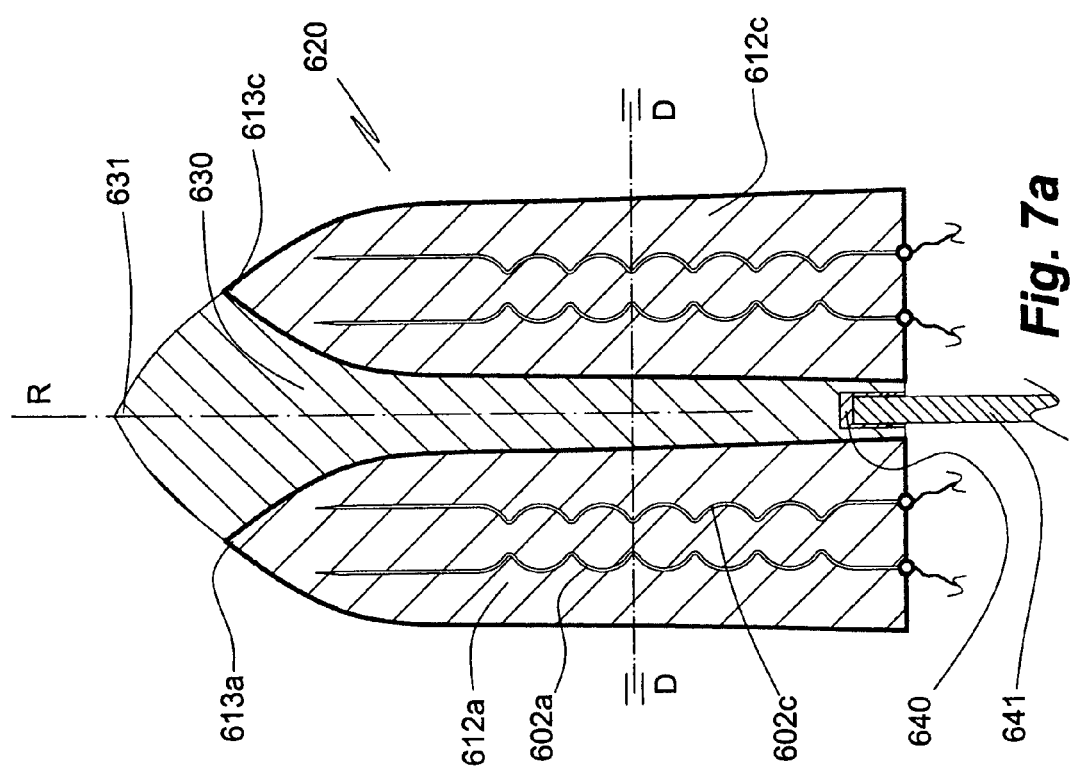
FIG. 7a is a longitudinal section through a first embodiment of the electrode bundle array of the invention comprising four matrix-embedded electrode bundles of FIGS. 5a, 5b.

A distally pointed 631 array 620 of electrode bundles of the invention comprises four matrix-embedded electrode bundles disposed equidistantly and rotationally symmetrically (four-fold rotational symmetry) from an array axis R of the invention (FIGS. 7a, 7b). The array 620 comprises four electrode bundles of the kind illustrated in FIGS. 5a, 5b, of which only the bodies 602a-602d of the four electrodes of the first bundle are identified by reference numbers. The electrode bundles are embedded in solid dissolvable matrices 612a-612d, respectively. The four matrix-embedded electrode bundles are disposed in parallel with their tips 613a-613d pointing in the same, distal direction. The matrix-embedded electrode bundles are joined by a glue 630, which is dissolvable in an aqueous environment. The glue 630 is preferably different in composition and dissolution or swelling rate from the material of the embedding matrices 612a-612d. The material of the embedding matrices may be one and the same but it is also conceivable to use material(s) with different dissolution or swelling rates for one or more of them. The array 620 is provided with a female coupling member 640 disposed centrally in the glue 630 at its proximal flat end face. The coupling member 640 is designed to releasingly receive a manipulation rod 641 for insertion of the array 620 into tissue.

Figure 8C:
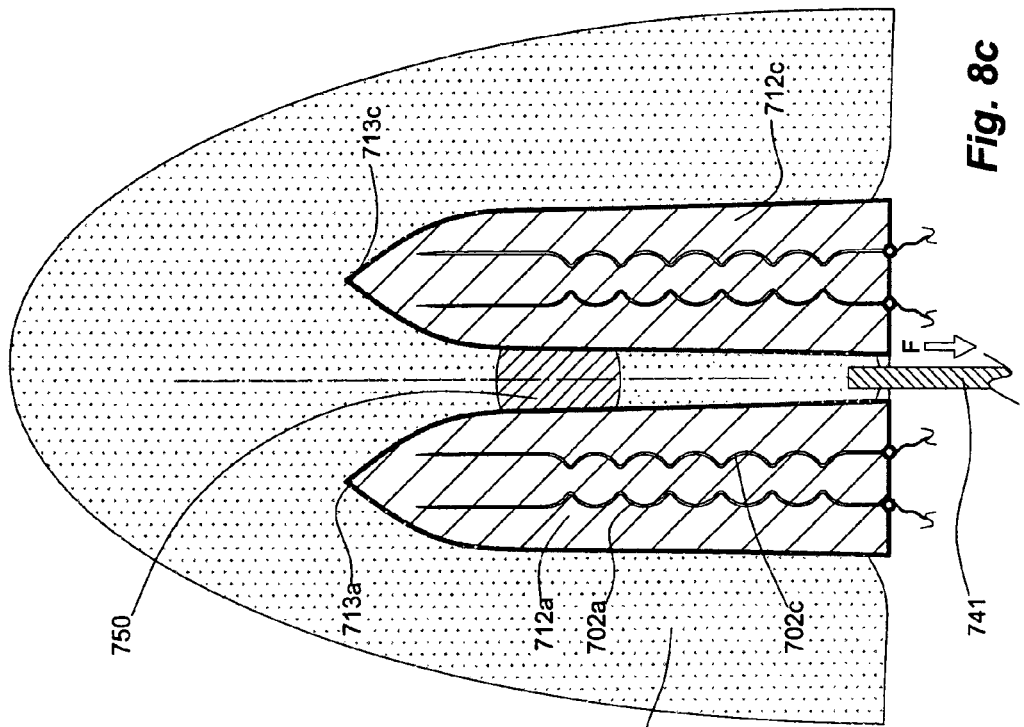
Figure 8B:
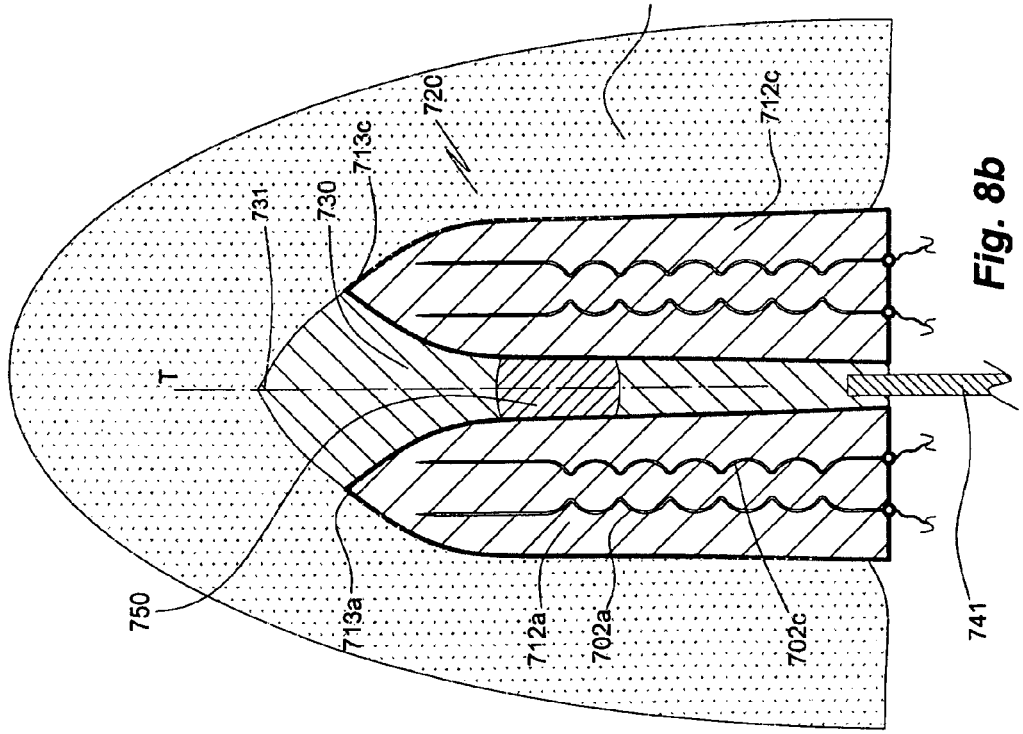
Figure 8F:
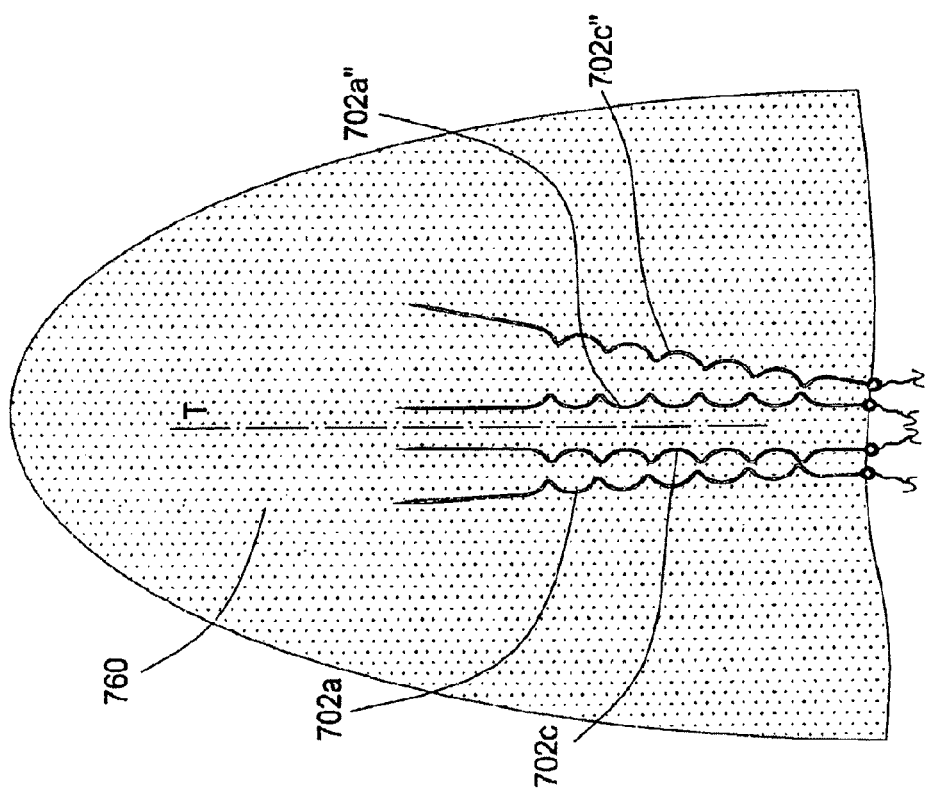

Another distantly pointed 731 electrode bundle array 720 of the invention of same symmetry as the array of FIGS. 7a, 7b is shown in FIGS. 8, 8a. In addition to the water soluble glue 730 connecting the electrode bundles of the array 720, the latter additionally comprises a swelling plug 750 disposed centrally in respect of the array axis T and extending from there in a radial direction to the innermost wall sections of the matrix bodies 712a-d each comprising a matrix-embedded electrode bundle with four electrodes each, each electrode having an extendable electrode body 702a-d, etc., whereas, in an axial direction the proximal and distal faces of the plug 750 abut the glue 730 by which the four matrix-embedded electrode bundles are kept in place. An insertion rod 741 is embedded in the central proximal portion of the glue 730. FIGS. 8b-8f illustrate the fate of the array 720 after insertion into soft tissue 760. FIG. 8b shows the situation immediately upon insertion of the array 720 into the tissue 760. The array 720 is still intact. FIG. 8b shows the situation about 2 minutes upon insertion during which period the glue 730 has dissolved in the aqueous environment of the tissue 760. Reference number 760 represents both soft tissue and fluid formed by dissolution of the glue 730. The matrix bodies 712a-d are now separated, except for a possible adhesion to the swelling plug 750. Next the swelling plug 750, now in contact with tissue fluid, begins to swell. The situation after considerable swelling of the plug 750 is shown in FIG. 8d. The swelling plug 750 is of a material that first swells and later dissolves in contact with aqueous body fluids. It is, for instance, made of gelatin. The swelling of the plug makes the matrix-embedded electrode bundles move radially apart, the result of which is shown in FIG. 8e. Finally, the matrix bodies 712a-712d are slowly dissolving in body fluid, which results in the electrodes 702a, 702c of the first electrode bundle, the electrodes of the third electrode bundle 702a", 702c", and the electrodes of the other electrode bundles becoming disposed in the tissue, as shown in FIG. 8f.

The third embodiment of the electrode bundle of the invention shown in FIG. 13 comprises four electrodes with extendible electrode bodies 802a, 802c attached to bases 804a, 804c. The bundle is embedded in a dissolvable matrix body 812 narrowing towards its distal tip 813. The electrode bases 804a, 804c are moulded in an electrode holder disk 807 from which their rear portions provided with conductors 806a, 806c extend. The electrode holder disk 807 is made of a non-conducting polymer material. This embodiment allows to keep the proximal portions of the electrodes at a desired distance, whereas their distal portions can move more freely.

Figure 9:
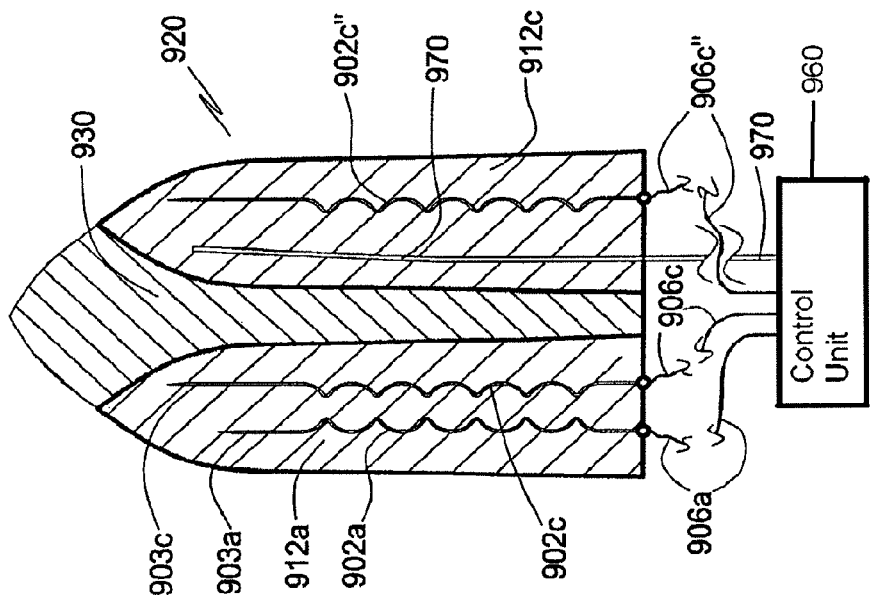
FIG. 9 is a third embodiment of the electrode bundle array of the invention, in a longitudinal section corresponding to that of FIG. 8.

A third embodiment of the electrode bundle array 920 of the invention is shown in FIG. 9. It differs from the electrode bundle array 620 of FIGS. 7a, 7b in that electrodes of the invention with tip sections 903a, 903c of different length and electrode bodies 902a, 902c of same length are comprised by a first electrode bundle embedded in a matrix 912a, and that a third electrode bundle embedded in a matrix 912c comprises an electrode of the invention having an electrode body 902c'' and an optical fibre 970 disposed in parallel with the electrode. The array 920 comprises four matrix-embedded electrode bundles of which however only two are shown in FIG. 9. Electrodes of the array shown connected via thin flexible conductors 906a, 906c, 906c'' to a control unit 960 by which they may be powered or to which they may transmit electrical nerve signals. The optical fibre 970 is shown connected to the central unit which may comprise a light source for sending radiation through the fibre into the tissue in which the fibre 970 is implanted or which may comprise means for detecting radiation emanating from the tissue received via the fibre 970.

FIGS. 10-12 illustrate further preferred embodiments of the electrode of the invention with modified tip sections.

The electrode 1001 of FIG. 10 comprises an extendable oblong electrode body 1002 and a tip section 1003 from which short tags 1011-1011''' extend radially/distally and spaced along the tip section 1003.

The electrode 1101 of FIG. 11 comprises an extendable oblong electrode body 1102 and a tip section 1103 from which doubly curved tags 1111-1111'''' extend about radially and spaced along the tip section 1103.

The electrode 1201 of FIGS. 12, 12a comprises an extendable oblong electrode body 1202 and a tip section 1203 from a radial plane of which twenty-four rearwards curved tags, of which only the first and the twelfth tag 1211-01, 1211-13 extend in an umbrella-like configuration.

The electrode bundle array 1320 of the invention of FIG. 14 comprises four electrode bundles of the kind shown in FIG. 13. In the sectional view of FIG. 14 only two of them can be seen. Except for matrix bodies 1312a, 1312c and electrode holder disks 1307, 1307'' only the elements of the first bundle, which comprises four electrodes, are provided with reference numbers. Only two of the electrodes of the first bundle are visible in the figure, the first electrode comprising an electrode body 1302a and the third electrode comprising an electrode body 1302c. They are embedded in a dissolvable, substantially conical matrix body 1312a that narrows towards its distal tip, which is however not shown. Their bases 1304a, 1304c are moulded in an electrode holder disk 1307 of a non-conducting polymer material. The electrode bundle holders 1307, 1307'' are adhesively mounted (not shown) on an array holder disk 1335 with their proximal faces abutting the distal face of the disk 1335. To allow the leads 1306a, 1306c of the electrodes to pass through the array holder disk 1335 the latter is provided with through bores 1337a, 1337c facing the electrode bases 1304a, 1304c. The electrode bundles are disposed symmetrically in respect to and equidistantly from the array long axis (not shown). Their spacing allows a central cylindrical portion 1336 extending from the distal face of the array holder disk 1335 to be disposed between them. A central bore in the proximal face of the cylindrical portion 1336 is arranged for releaseably holding a manipulation rod 1341 by which the array 1320 can be inserted into soft tissue. The remaining interstice between the electrode bundles is filled with a biocompatible glue 1330 soluble in an aqueous environment.

Materials and Dimensions

Electrode dimensions. The electrodes of the invention have a suitable diameter of from $10^{-4}$ to $10^{-7}$ m, in particular of from 0.5 to 25 µm. A larger wire diameter, such as up to $1.5 \times 10^{-3}$ m may be used in case a gross stimulation/recording paradigm is used, for example to produce lesions in soft tissue. Their diameter may change over their length to facilitate insertion into the tissue, in particular the electrode can be tapering towards their distal end. Their distal end can be sharp or blunt but a sharp tip is preferred in case of the electrode being used for recording of electrical activity. Their distal part may even have a diameter smaller than $10^{-7}$ m.

The surface of electrodes may be smooth or not or partially smooth and partially not smooth, that is, rough. An uneven or rugged surface close to the electrode tip is preferred for improving the anchoring properties and for reducing the impedance of the electrode tip. The electrode of the invention is preferably insulated except for at portions extending from their proximal and distal ends. However, the electrode body may also be equipped with means to allow stimulation/recordings at multiples sites within the tissue. Such means may, for example, consist of protruding ultra-thin filaments, or portions with a rough or uneven surface occupying a length of 10 µm or more. Such regions are not electrically insulated if an electrical contact with the tissue is intended. They may also serve as anchoring means and, in addition, as for electrical stimulation/recording. If electrical stimulation of a larger volume of tissue is intended, it is alternatively preferred not to insulate a larger portion extending from the electrode tip, such as a length of up to 100 µm or even up to 1 mm. Suitable for insulation of the electrode wires are, for instance, glass, polyvinyl formal, silicon rubber, water-insoluble lacquer.

An electrode of the invention with a branching distal end section can be made from a multi-strand silk thread, from which individual strands of a diameter from about 1 µm to about 5 µm are arranged so as to fan out like an umbrella at one end of the thread. In this fanned-out configuration the electrode is covered with an electrically conductive material, in particular a metal, by conventional evaporation or sputtering techniques. The electrode is then covered by insulating material except at short terminal sections of the fanned-out strands. A manner of making an electrode of the invention comprising branches extending from the electrode core at a desired point or section comprises intertwining short pieces of thin metal wire or of polymer threads with a twinned electrode core. The pieces of metal wire or polymer thread are disposed about perpendicularly or in skew directions in respect of a silk core being spun from several silk filaments so as to make the pieces of metal wire or polymer thread held between the twinned filaments of the silk core like in tinsel fringe (Lametta); the use of metal wires in this method additionally provides a means for making multi-point electrodes.

Electrode shape. An important feature of the present invention is that the distance from the distal tip to the proximal base of the electrode can be repetitively and reversibly increased and decreased without rupture of the electrode so as to permit the wire to smoothly follow non-uniform movements in surrounding soft tissue, such as may occur in the vicinity of arterial or venous vessels, the heart or the lungs or between soft and hard tissue. This is achieved by equipping the electrode with multiple bends, which may follow a given pattern or not. The electrodes thus can have a wavy, curly, tortuous, spiral or otherwise not straight configuration, which allows the distance from the proximal base to the distal tip to be easily increased/decreased by at least 1%, but preferably by at least 5% when force is exerted along the wire. For example, the distance from tip to base of an electrode of 1 mm in length can be easily increased/decreased by at least 10 µm, and even by 50 µm or more.

It is preferred to use a smooth bending pattern, such as a wavy or spiral pattern. A pattern characterized by abrupt bends is less preferred, since the forces caused by increasing/decreasing the distance between the tip and the base of the electrode should not substantially affect particular sites on or short sections along the electrode body, but should rather affect larger sections. This will increase the endurance of an electrode exposed to continuous changes in length by the movement of surrounding living tissue.

Electrode materials. To approach the ratio of electrode density to tissue density, and thereby reduce the difference in inertia between the electrode and the tissue, the electrode of the invention preferably comprises a core a light and strong nonconductive material such as natural protein fibre, for instance silk, or polymer fibre covered by an electrically conductive material. Alternatively a tubiform supportive material filled with an electrically conductive material such as a metal, in particular a noble metal or a noble metal alloy, but also carbon may be used. Other examples of useful nonconductive core or tubiform supporting materials are glass and ceramic. The electrically conductive material can be deposited on the support material by conventional sputtering or evaporation techniques. Although not preferred, the electrode of the invention can optionally comprise an electrically conductive metal core of, in particular, gold, platinum, titanium, stainless steel, an alloy comprising more than 30% by weight of noble metal such as iridium, the combination of platinum and iridium, and tungsten, but also of an electrically conductive polymer.

Matrix materials. The electrode of the invention is embedded in one or more biocompatible matrix materials that differ in their dissolution rate. For applications where the wires are intended to follow straight lines during insertion or to keep their configuration after insertion, it is preferred to use one embedding material. For applications where the distal parts of the electrodes are intended to unfold in the target tissue it is preferred to use at least two different embedding materials, one more short lasting, below referred to as matrix material X, and another longer-lasting, below referred to as matrix material Y. Suitable matrix materials include carbohydrate and/or a proteinaceous material but also, for instance, gum Arabic and poly-glycolic acid. Matrix material X used for embedding a distal end portion of the electrode has a dissolution rate at a temperature of 37° C. in body fluid, such as plasma or interstitial fluid, that allows an electrode embedded therein to become unrestrained in regard of its displacement in respect of neighbouring electrodes within a short period of time, in particular within 5 seconds to 3 minutes. Matrix material Y is one having a corresponding dissolution rate that allows an electrode embedded therein to become unrestrained in regard of its displacement in respect of neighbouring electrodes within from 30 seconds to 10 minutes or more but in any event at a later point in time than the moment at which electrode's distal end portion becomes unrestrained in its (lateral) displacement. Longer dissolution times for matrix material X, such as up to 20 minutes, and correspondingly longer dissolution times for matrix material Y may be used in a slow insertion procedure, for instance when inserting an electrode array deep into tissue.

Suitable materials for matrix material X include disaccharides such as sucrose boiled in water for 10-30 minutes or longer; thereby dissolution times of 1-3 minutes are achieved. Other materials suitable as matrix material X include gelatin and gelatine based materials that had been dissolved in water of 40-50° C. and then allowed to dry.

A suitable material for use as matrix material X can be obtained by repeatedly boiling and cooling an aqueous solution containing a sugar or a mixture of sugars selected from sucrose, lactose, mannose, maltose, and an organic acid selected from citric acid, malic acid, phosphoric acid, tartaric acid. Combinations of sugars and organic acids render a range of dissolution times.

Gelatin may also be used as a matrix material. It is well known that different types of gelatine or gelatine based materials have different dissolution rates. Hence, by selecting a proper combination of two types of gelatin for matrix material X and matrix material Y, it is possible to achieve faster dissolution time of the distal matrix portion of an electrode bundle or array embedded in a bisectional dissolvable matrix than of the respective proximal matrix portion. The use of a sugar-based matrix material for the distal matrix portion and of a gelatine-based matrix material for the proximal matrix portion or vice versa is also possible, as well as the gelatin for a distal matrix material and of gum Arabic for proximal matrix material. The selection of further useful combinations of matrix materials, such as various types of natural gums, is within the easy reach of a person skilled in the art.

Optionally, matrix materials with substantially longer dissolution times, such as modified collagen, cellulose derivatives, modified starch or other biocompatible materials, such as poly-glycolic acid can also be used in applications comprising a slow insertion procedure. For example, in cases when the track line of the electrode array is assessed repetitively during insertion by, for instance, X-ray imaging, and/or the track line is modified by passing current through contractile filaments comprised by the electrode array, the time for completion of the insertion procedure may take a longer time.

If an electrode, an electrode bundle or electrode array of the invention is to be inserted into tissue located immediately below the skin or mucosa or near the surface of the brain or the spinal cord or another tissue, such as to a tissue depth of less than 2 mm, it may suffice to use a single matrix material also when the electrodes are meant to unfold in the tissue, in particular a matrix material X, since only the distal part of the electrode array that is unfolding may be disposed in the tissue.

Optionally the matrix-embedded electrode, electrode bundle or electrode array of the invention can be covered, completely or in part, by a biocompatible gliding agent to reduce friction during insertion into tissue. The gliding agent can also be one that retards the access of body fluid to the matrix material and thereby decelerates the dissolution/degradation thereof. Useful gliding agents include glycerol monopalmitate, glycerol dipalmitate, glycerol monostearate, glycerol distearate, palmityl alcohol, stearyl alcohol. A thin coat of gliding agent can be applied on the matrix body by, for instance, spraying the body with a solution of the agent in ethanol or ethyl acetate.

Exemplary Uses

Preferred uses of the electrode of the invention as well as bundles of the electrode of the invention and arrays of the electrode of the invention and/or of bundles of the electrode of the invention are described in the following.

Clinical use. For aiding patients after brain/spinal damage by recording signals from remaining neurons in case of, for instance, stroke or degenerative disease and/or stimulating neurons to compensate for lost functions. Similar uses are possible in animals. In particular: pain relief by stimulation of analgesic brain stem centres, such as nuclei in the periaqueductal grey substance; relief or decrease of tremor in Parkinson's disease, choreatic and other involuntary movements by stimulation within the basal ganglia or associated nuclei; boosting memory by stimulation of cholinergic and/or monoaminergic nuclei in case of Alzheimer's disease or other degenerative diseases; control of mood, aggression, anxiety, phobia, affect, sexual over-activity, impotence, eating disturbances by stimulation of limbic centres or other brain areas; rehabilitation of patients after stroke or damage of the brain/spinal cord by stimulation of remaining connections in the cortex cerebri or descending motor pathways; re-establishment of control of spinal functions such as bladder and bowel emptying after spinal cord injury by stimulating relevant parts in the spinal cord; control of spasticity by stimulation of inhibitory supraspinal descending centres or appropriate cerebellar areas; re-establishment of somatosensory, auditory, visual, olfactory senses by stimulation of relevant nuclei in the spinal cord and the brain.

Examples where recording is combined with stimulation include: monitoring of epileptic attacks by electrodes implanted into the epileptic focus—coupled to a system that deliver antiepileptic drugs or electrical pulses; compensating for lost connections in the motor system by recording central motor command and stimulating the executive parts of the motor system distal to the lesions; recordings of blood glucose levels to control the release of hormones. Implanted electrodes of the invention may also be used for locally lesioning tissue by passing current of sufficient magnitude through the electrodes. This can be useful if a tumour or an abnormally active or epileptogenic nervous tissue has to be lesioned.

Use in research. To study the normal and pathological functions of the brain and spinal cord, it is necessary to be able to record neuronal activity and, at the same time, interact with the undisturbed CNS. For this purpose, the electrodes, electrode bundles and arrays of electrode bundles of the invention will have to be implanted in CNS for a long time. Due to their design and dimensions they can be left securely in the CNS for a very long time, also during development when tissue volume is gradually increasing. They can, either through wire-connections or telemetric equipment, communicate with measurement equipment of various kind, such as amplifiers, stimulators and computers. They can also be used for stimulation or for a combination of recording and stimulation. For example, they can be used to monitor activity in pain related pathways or in pain control systems in the brainstem or elsewhere in animals during tests of potential analgesics.

Use as an interface for interaction with computers and neuroprosthetic devices. In patients with damage to the peripheral nervous system, it can be useful to record command signals from CNS. These signals can then be interpreted by computer programs and used to guide activity in neuroprostheses, such as artificial hands or feet, guide stimulation of muscles and organs such as the bladder and bowel.

Use in controlling the function of endocrine and exocrine organs. In patients with a deficient hormone secretion or regulation, the electrode, electrode bundle or array of electrodes and/or electrode bundles of the invention may be used to control the secretion of hormones from exocrine or endocrine organs.

What is claimed is:

1. A medical electrode comprising:
    a base section,
    a tip section,
    an electrode body disposed between the base section and the tip section,
    the electrode body including one of:
        (a) an electrically conducting core and an insulating layer on the core, or
        (b) an electrically non-conducting core, an electrically conducting layer on the core and an insulating layer on the electrically conducting layer;
    the electrode body further including portions configured for movement relative to each other when implanted in or inserted into soft tissue, so as to increase or decrease their distance along the electrode, and
    a substantially rigid biocompatible matrix that is soluble or biodegradable in a body fluid, at least the tip section and the electrode body embedded in the matrix, the matrix forming a matrix body of a shape configured to follow a straight insertion track line when inserting the electrode deep into soft tissue.

2. The electrode of claim 1, wherein the base section, tip section, electrode body and substantially rigid biocompatible matrix form the matrix body.

3. The electrode of claim 2, wherein the electrode body comprises one or several passages through the insulating layer perpendicular to the core permitting electrical contact with the electrically conducting core or the electrically conducting layer.

4. The electrode of claim 2, wherein the electrode body is embedded in the matrix in a configuration in which its length is greater by 2 percent or more than the distance between its ends.

5. The electrode of claim 1, further comprising an anchor disposed at the tip section.

6. The electrode of claim 5, wherein the anchor is embedded in the matrix.

7. The electrode of claim 1, wherein the matrix body comprises two sections differing in their dissolution or degradation rate.

8. The electrode of claim 1, wherein a diameter of the electrode body is from about $10^{-7}$ to about $10^{-4}$ m.

9. The electrode of claim 1, further comprising a dissolution retardation coating on the matrix body.

10. A medical electrode bundle comprising:
    two or more bundle electrodes, each bundle electrode including:
    base section,
    a tip section,
    an electrode body disposed between the base section and the tip section,
    the electrode body including one of:
        (a) an electrically conducting core and an insulating layer on the core, or
        (b) an electrically non-conducting core, an electrically conducting layer on the core and an insulating layer on the electrically conducting layer; and
    portions of the electrode body configured for movement relative to each other when implanted in or inserted into soft tissue, so as to increase or decrease their distance along the electrode, and
    a substantially rigid biocompatible matrix that is soluble or biodegradable in a body fluid, at least the tip section and the electrode body embedded in the matrix, the matrix forming a bundle matrix body of a shape configured to follow a straight insertion track line when inserting the electrode deep into soft tissue.

11. The electrode bundle of claim 10, wherein the body fluid is an aqueous body fluid.

12. The electrode bundle of claim 11, wherein each bundle electrode comprises an anchor disposed at the tip section.

13. The electrode bundle of claim 10, wherein the bundle matrix comprises two sections differing in their dissolution or degradation rate.

14. The electrode bundle of claim 10, wherein the electrode body is embedded in the bundle matrix in a configuration in which its length is greater by 2 percent than the distance between its ends.

15. The electrode bundle of claim 10, wherein the diameter of the electrode body is from about $10^{-7}$ m to about $10^{-4}$ m.

16. The electrode bundle of claim 10, further comprising a dissolution retardation coating on the bundle matrix body.

17. The electrode bundle of claim 10, further comprising a base plate of a non-conducting material at which bases of bundle electrodes are mounted.

18. The electrode bundle of claim 10, comprising one or more optical fibres.

19. A medical electrode bundle array comprising two or more electrode bundles of claim 10, at least partially embedded in a substantially rigid biocompatible array matrix that is soluble or biodegradable in a body fluid, the array matrix foaming an array matrix body of a shape permitting following of a straight insertion track line when inserting the array deep into soft tissue.

20. The array of claim 19, wherein the dissolution or degradation rate of the array matrix in said body fluid is higher than the dissolution or degradation rate of the bundle matrix in the same fluid.

21. The array of claim 19, comprising a dissolution or degradation retardation coating on the array matrix body.

22. A method of inserting or implanting a flexible medical electrode in tissue in a desired configuration, comprising:
    providing the electrode of claim 1;
    inserting or implanting the electrode into/in tissue;
    allowing the matrix to dissolve or to be degraded in situ.

23. A method of inserting or implanting a medical electrode bundle in tissue in a desired configuration, comprising:
    providing the electrode bundle of claim 10;
    inserting or implanting the matrix embedded electrode bundle into/in tissue;
    allowing the matrix to dissolve or be degraded in situ.

24. The method of claim 23, wherein the matrix comprises a proximal section of lower dissolution or degradation rate and a distal section of higher dissolution or degradation rate.

25. A method of inserting or implanting an array of medical electrode bundles comprising:
    providing an array of electrode bundles of claim 19;
    inserting the array into tissue; and allowing the array and bundle matrices to dissolve or be degraded in situ.

* * * * *

UNITED STATES PATENT AND TRADEMARK OFFICE
CERTIFICATE OF CORRECTION

PATENT NO. : 8,386,006 B2  Page 1 of 1
APPLICATION NO. : 12/747343
DATED : February 26, 2013
INVENTOR(S) : Jens Schouenborg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 323 days.

Signed and Sealed this

First Day of September, 2015

Michelle K. Lee
*Director of the United States Patent and Trademark Office*